US00PP16988P2

(12) United States Plant Patent
Lindsey

(10) Patent No.: US PP16,988 P2
(45) Date of Patent: Aug. 15, 2006

(54) ***ABELIA* PLANT NAMED 'KALEIDOSCOPE'**

(50) Latin Name: *Abelia×grandiflora*
Varietal Denomination: Kaleidoscope

(76) Inventor: Randall Dale Lindsey, 610 Redah Ave., Locust, NC (US) 28097

( * ) Notice: Subject to any disclaimer, the term of this patent is extended or adjusted under 35 U.S.C. 154(b) by 96 days.

(21) Appl. No.: 11/053,533

(22) Filed: Feb. 7, 2005

(51) Int. Cl.
*A01H 5/00* (2006.01)

(52) U.S. Cl. ..... Plt./226
(58) Field of Classification Search ..... Plt./226
See application file for complete search history.

(56) References Cited

U.S. PATENT DOCUMENTS

PP8,472 P * 11/1993 Gwaltney ..... Plt./226
PP9,698 P * 11/1996 Morales-Martinez et al. ..... Plt./226
PP15,203 P2 * 10/2004 Crowder ..... Plt./226

OTHER PUBLICATIONS http://www.planthaven.com/pdfs/ABELIA%20kaleidoscope.pdf#search=‘abelia%20kaleidoscope’.*

* cited by examiner

*Primary Examiner*—Kent Bell
*Assistant Examiner*—W. C. Haas

(57) ABSTRACT

A new cultivar of *Abelia* named 'Kaleidoscope' that is characterized by dense compact habit, fragrant white flowers, and variegated foliage that exhibits seasonal color changes from green and golden-yellow, to orange and fiery-red. In combination these traits set 'Kaleidoscope' apart from all other existing varieties of *Abelia* known to the inventor.

5 Drawing Sheets

Botanical designation: *Abelia×grandiflora.*
Variety denomination: 'Kaleidoscope'.

BACKGROUND OF THE INVENTION

The present invention relates to a new and distinct cultivar of *Abelia* grown as an ornamental plant for use in the landscape. The new cultivar is known botanically as *Abelia× grandiflora* and will be referred to hereinafter by the cultivar name 'Kaleidoscope'.

'Kaleidoscope' was discovered by the inventor in 1997 as a single variegated branch sport on an individual *Abelia× grandiflora* 'Little Richard' (unpatented). The inventor, who manages plant propagation on a nursery in Marshville, N.C., selected 'Kaleidoscope' from an individual plant of *Abelia* 'Little Richard' within a crop of 'Little Richard'. The parent plant is *Abelia×grandiflora* 'Little Richard'.'Kaleidoscope' is distinguishable from 'Little Richard' by dense compact habit, smaller size, and variegated foliage. *Abelia* 'Little Richard' exhibits a larger growth habit and solid-green leaves.

'Kaleidoscope' is an ornamental shrub of dense compact habit and variegated foliage. From spring through summer, and into fall and winter, the foliage colors on an individual plant change from green and golden-yellow to orange and fiery-red. Fragrant white flowers appear in mid summer and persist into fall adding a striking contrast against the reddish-purple stems. Light levels influence foliage color and full sun enhances vibrancy of the colors.

Other than the non-variegated parent plant, *Abelia* 'Little Richard', the three closest comparison plants known to the Inventor are the variegated *Abelia* cultivars *Abelia× grandiflora* 'Sunrise' (U.S. Plant Pat. No. 9,698) and

*Abelia×grandiflora* 'Conti' (U.S. Plant Pat. No. 8,472) and *Abelia×grandiflora×chinensis* 'Mardi Gras' (U.S. Plant Pat. No. 15,203).

The leaves of 'Sunrise', 'Conti', and 'Marti Gras', are predominantly green (that is, green coloration occupies approximately 70% to 85% of entire leaf surface), with relatively uniform and slender white or cream-yellow margins occupying approximately 30% to 15% the entire leaf surface.

The leaves of 'Kaleidoscope' consists of smaller green blotches which occupy approximately 50% of the entire leaf surface, surrounded by yellow (spring and summer) or orange and red margins which occupy approximately 50% of the leaf surface area.

'Kaleidoscope' is most readily distinguished from its parent, 'Little Richard' and from the variegated cultivars 'Sunrise', 'Conti' and 'Mardi Gras' by its striking and vibrant fall and winter foliage color that is a mix of golden-yellow, orange and fiery-red.

'Kaleidoscope' (and its parent 'Little Richard') may also be distinguished from other cultivars of *Abelia×grandiflora* by plant habit and plant density. 'Kaleidoscope' and 'Little Richard' appear to be more determinate, requiring minimal pinching or pruning to retain their close dense mounding habit which obscures the stems. 'Sunrise', 'Conti' and 'Mardi Gras' each exhibit stronger apical dominance which results in extended shoot growth and more visibility of their stems.

'Kaleidoscope' was first asexually propagated in 1997 by the inventor in North Carolina. Asexual propagation was accomplished using softwood cuttings. Since that time, under careful observation, the distinguishing characteristics of 'Kaleidoscope' have been determined stable and uniform, and are reproduced true to type in successive generations.

SUMMARY OF THE INVENTION

The following represent the distinguishing characteristics of the new *Abelia×grandiflora* cultivar 'Kaleidoscope'. In combination these traits set 'Kaleidoscope' apart from all other existing varieties of *Abelia* known to the inventor. 'Kaleidoscope' has not been tested under all possible conditions and phenotypic differences may be observed with variations in environmental, climatic, and cultural conditions, however, without any variance in genotype.

1. *Abelia×grandiflora* 'Kaleidoscope' exhibits variegated foliage.
2. The foliage of *Abelia×grandiflora* 'Kaleidoscope' displays seasonal color changes, from green and golden-yellow, to orange and fiery-red.
3. The foliage color of *Abelia×grandiflora* 'Kaleidoscope' is influenced by light levels and full sun enhances vibrancy of the colors.
4. *Abelia×grandiflora* 'Kaleidoscope' exhibits reddish-purple stems.
5. *Abelia×grandiflora* 'Kaleidoscope' is 76 cm. in height and 121 cm. in width at maturity.
6. *Abelia×grandiflora* 'Kaleidoscope' exhibits fragrant white flowers that bloom from mid summer into fall
7. *Abelia×grandiflora* 'Kaleidoscope' exhibits dense compact habit.
8. *Abelia×grandiflora* 'Kaleidoscope' is suitable for use as a low accent plant, mass plantings in the landscape, and as a container plant.
9. *Abelia×grandiflora* 'Kaleidoscope' performs well in acidic, well-drained, moist soils.
10. *Abelia×grandiflora* 'Kaleidoscope' is hardy to USDA Zone 5 as an herbaceous perennial and stem hardy to USDA Zone 6.

BRIEF DESCRIPTION OF THE DRAWINGS

The accompanying color drawings illustrate the overall appearance of the new *Abelia* cultivar 'Kaleidoscope' showing the colors as true as it is reasonably possible to obtain in colored reproductions of this type. Colors in the drawings may differ from the color values cited in the detailed botanical description, which accurately describe the actual colors of the new variety 'Kaleidoscope'.

The drawing labeled

The drawing labeled

The drawing labeled

The drawing labeled

The drawing labeled

Figure 1:
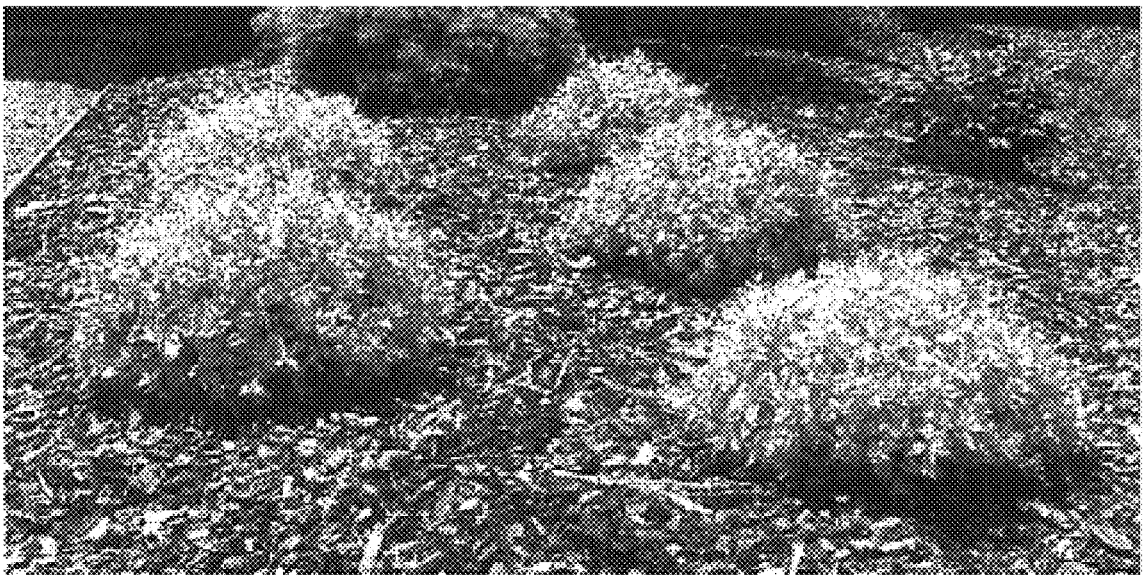
FIG. 1 shows five two-year old plants of 'Kaleidoscope' planted in the landscape in North Carolina and exhibiting the typical dense, compact mounding habit of 'Kaleidoscope'.
Figure 2:
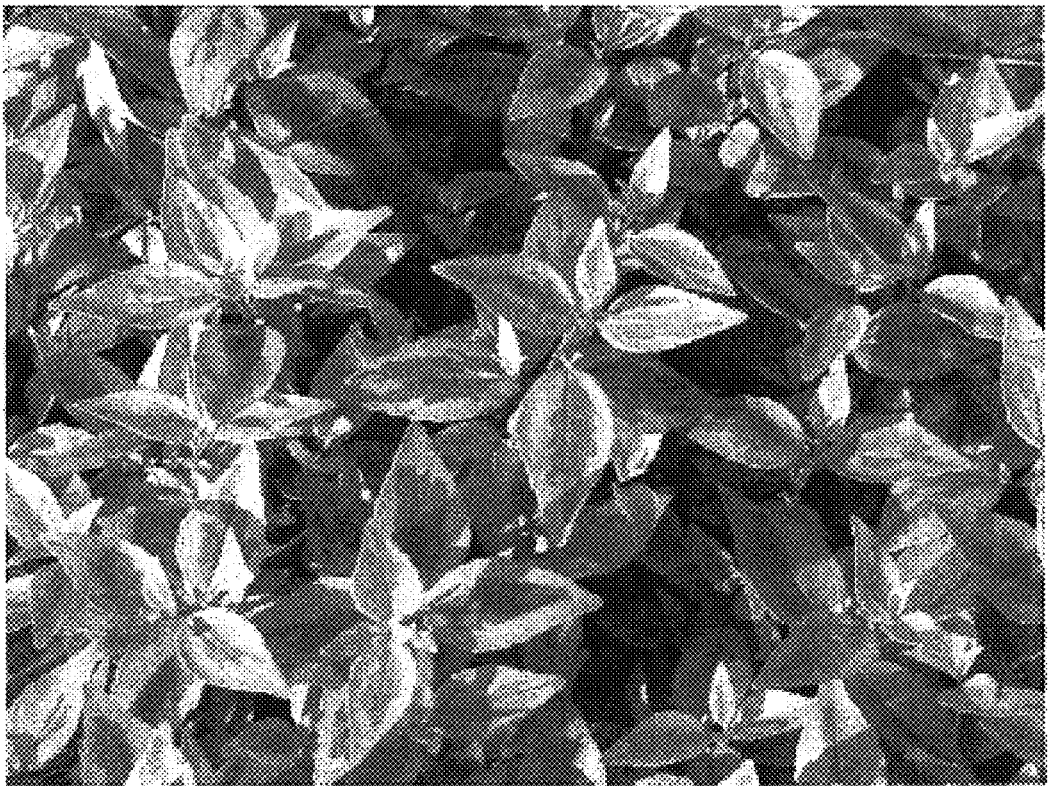
FIG. 2 is a close-up view of the variegated foliage in its yellow and green spring growth.
Figure 3:
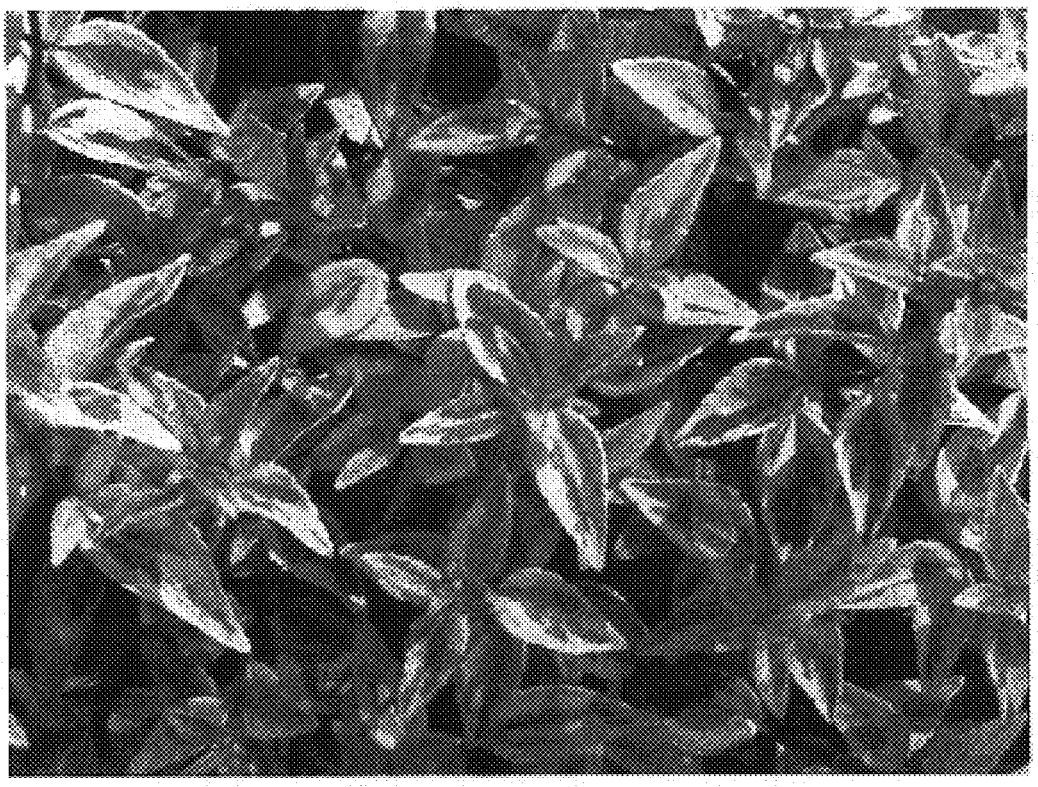
FIG. 3 is a close-up view of the variegated foliage in its summer growth which exhibits golden-yellow, green and reddish tones.
Figure 4:
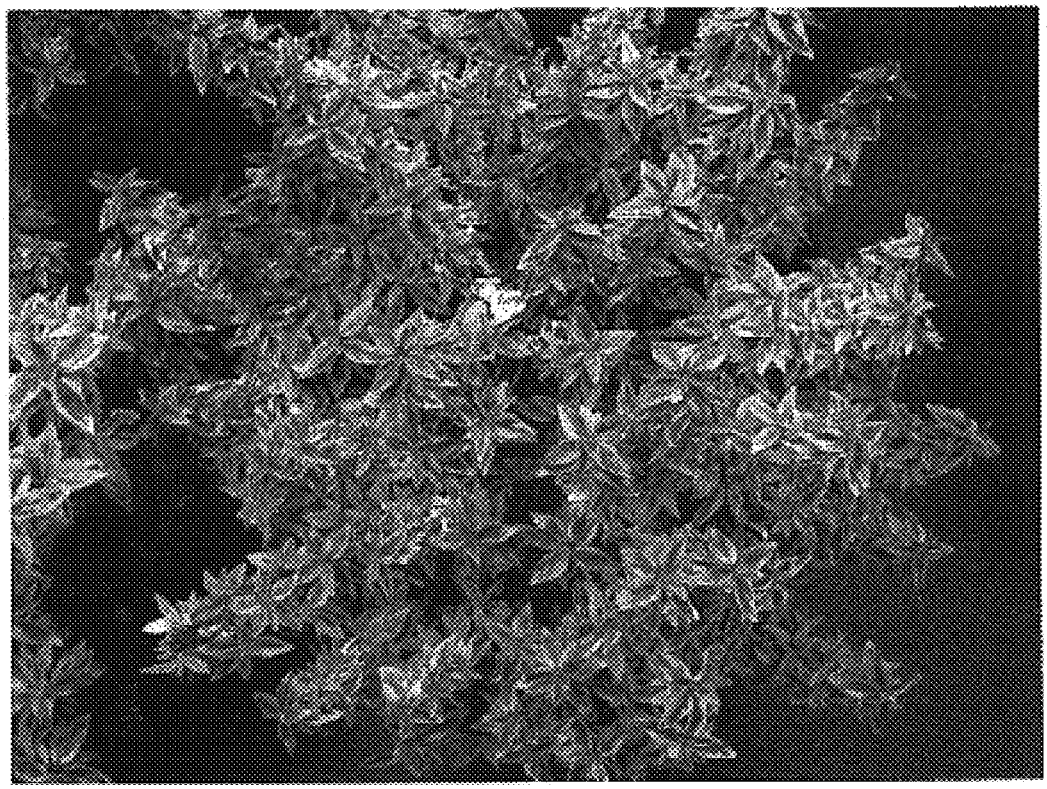
FIG. 4 illustrates a whole plant of 'Kaleidoscope' in its fall growth and exhibiting the mix of golden-yellow, orange and fiery-red fall foliage.
Figure 5:
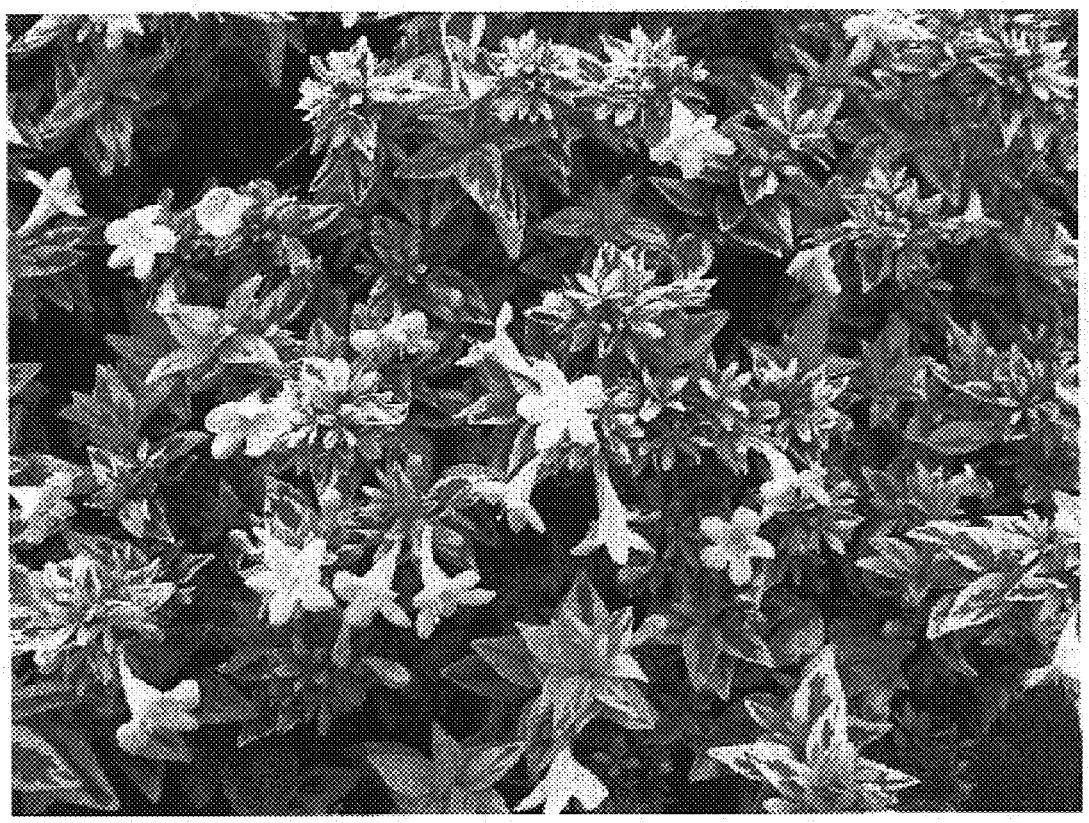
FIG. 5 is a close-up view of 'Kaleidoscope' illustrating the flowers that bloom from mid summer into fall.

The drawings have been made from photographs taken by conventional techniques and although foliage colors may appear different from actual colors due to light reflectance, they are as accurate as possible by conventional photography.

BOTANICAL DESCRIPTION OF THE PLANT

The following is a detailed description of the *Abelia× grandiflora* cultivar named 'Kaleidoscope'. Data was collected in Arroyo Grande, Calif. from plants grown in 2-liter containers out-of-doors in full sun. The plants are approximately 18-months-old. Color determinations are in accordance with the 2002 Edition of the Colour Chart of The Royal Horticultural Society, London, England, except where general color terms of ordinary dictionary significance are used. 'Kaleidoscope' has not been tested under all possible conditions and phenotypic differences may be observed with variations in environmental, climatic, and cultural conditions, however, without any variance in genotype. The growing requirements are similar to the species.

Botanical classification: *Abelia×grandiflora* 'Kaleidoscope'.
Genus: *Abelia.*
Species: *×grandiflora.*
Denomination: 'Kaleidoscope'.
Commercial classification: Ornamental shrub.
Common name: Glossy *abelia.*
Uses: Low accent plant and mass plantings in the landscape, and as a container plant.
Container size: Suggested container size is 1.5 to 2 liters for producing a one or two year old plant.
Cultural requirements: Plant in acidic and well-drained moist soil. Full sun enhances vibrancy of foliage color, but plants will grow in partial shade.
Parent: 'Kaleidoscope' was discovered as a single variegated branch sport on an individual *Abelia grandiflora* 'Little Richard' in a crop of 'Little Richard'.
Plant description:

*Blooming season.*—From mid summer into fall.
*Plant habit.*—Dense and compact.
*Vigor.*—Vigorous.
*Plant form.*—Mounding.
*Plant height* (*at maturity*).—Averages 76 cm when established in the landscape for three or four years.
*Plant width* (*at maturity*).—Averages 121 cm when established in the landscape for three or four years.
*Hardiness.*—Hardy to USDA Zone 5 as an herbaceous perennial and stem hardy to USDA Zone 6.
*Propagation.*—Softwood cuttings.
*Root system.*—Fibrous.
*Time to initiate roots.*—2 weeks are needed to produce roots on an initial cutting.
*Air temperature to develop roots on initial cuttings.*—An air temperature of 29° Centigrade is ideal to produce roots on initial cuttings.
*Crop time.*—4 months are needed to produce a liner plant in a 5 cm–10 cm plug or pot from an initial cutting. A liner plant can be potted and grown as a finished 1.5–2 liter container in a further 10–15 months.
*Seasonal interest.*—Fragrant white flowers from mid summer to fall, and a mix of vibrant leaf color from spring to fall and winter.
*Diseases and pests.*—May exhibit occasional moderate infection of *Botrytis* under conditions of high humidity and poor air circulation, as, for example, when plants are grown too closely together. Otherwise there are no serious diseases or pests known to the inventor.

*Growing requirements.*—Maintain good fertility to increase foliage retention in winter.

*Growing problems.*—None known to the inventor. Plant is easy to grow and requires little or no pruning to maintain dense compact mounding form.

Stem:

*Internode length.*—1.75 cm. between nodes.
*Stem diameter.*—2.50 cm. in diameter.
*Stem length.*—22 cm. in length.
*Shape.*—Cylindrical.
*Surface.*—Pubescent.
*Stem color.*—59A.

Foliage:

*Type.*—Evergreen to semi-deciduous.
*Leaf arrangement.*—Opposite and whorled.
*Leaf division.*—Simple.
*Leaf shape.*—Lanceolate.
*Leaf base.*—Rounded.
*Leaf apex.*—Acute.
*Leaf venation.*—Pinnate.
*Vein color* (*adaxial and abaxial surfaces*).—138D.
*Leaf surface* (*adaxial*).—Glabrous.
*Leaf surface* (*abaxial*).—Glabrous.
*Leaf appearance* (*abaxial surfaces*).—Semi-glossy.
*Leaf appearance* (*adaxial surfaces*).—Glossy.
*Leaf attachment.*—Petiolate.
*Petiole dimensions.*—3 mm. in length and 1 mm. in diameter.
*Petiole color.*—Colors 144A and 59A are both present on an individual plant.
*Petiole shape.*—Sulcate.
*Petiole surface.*—Glabrous.
*Leaf margin.*—Crenate.
*Leaf length.*—Leaves on an individual plant range from 1.5 cm. in length to 3.25 cm. in length.
*Leaf width.*—Leaves on an individual plant range from 6 mm. in width to 1.50 cm. in width.
*Spring leaf colors* (*adaxial surface*).—Centers of individual leaves are 144B and margins of individual leaves are 150C.
*Spring leaf colors* (*abaxial surface*).—Centers of individual leaves are 144B and margins of individual leaves are 150C.
*Fall and winter leaf color changes* (*adaxial surfaces*).—A mix of colors 137C, N34A, 34A, 34D, N170D.
*Fall and winter leaf color changes* (*abaxial surfaces*).—A mix of colors 137C, N34A, 34A, 34D, N170D.
*Foliar fragrance.*—None observed.

Flower:

*Inflorescence.*—Terminal panicles.
*Flower depth.*—2.50 cm. in depth.
*Flower diameter.*—2.25 cm in diameter.
*Corolla tube dimensions.*—2 cm. in length and 0.75 cm. in diameter.
*Corolla tube surface* (*inner surface*).—Pubescent.
*Corolla tube surface* (*outer surface*).—Glabrous.
*Corolla tube color* (*inner and outer surfaces*).—N155B.
*Petals.*—Five in number.
*Petal surface* (*adaxial surface*).—Pubescent.
*Petal surface* (*abaxial surface*).—Glabrous.
*Petal color* (*abaxial and adaxial surfaces*).—N155B.
*Petal apex.*—Rounded.
*Petal margins.*—Entire.
*Petal dimensions.*—0.75 cm. in length and 0.50 cm. in width.
*Petals fused or unfused.*—Basally fused.
*Flower shape.*—Funnelform.
*Flower color.*—N155B.
*Quantity of flowers.*—A range of 1–6 flowers per panicle.
*Persistent or self-cleaning.*—Self-cleaning.
*Color of peduncle.*—165C.
*Peduncle length.*—3 cm. in length.
*Peduncle diameter.*—2 mm. in diameter.
*Surface of peduncle.*—Puberulent.
*Pedicel color.*—182A.
*Pedicel dimensions.*—5 mm. in length and 0.75 mm. in width.
*Aspect.*—Facing outward and downward.
*Bud shape.*—Club-shaped.
*Bud color.*—155A.
*Bud surface.*—Puberulent.
*Bud dimensions.*—11 mm. in length and 4 mm. in diameter.
*Calyx shape.*—Stellate.
*Color of calyx.*—145A.
*Surface of calyx.*—Puberulent.
*Sepals.*—Five in number.
*Sepal dimensions.*—9 mm. in length and 3 mm. in width.
*Sepal margins.*—Entire.
*Sepal shape.*—Oblanceolate.
*Sepal apex.*—Acute.
*Sepal base.*—Cuneate.
*Sepal color.*—145A.
*Sepals fused or unfused.*—Unfused.
*Blooming period.*—Mid summer into fall.
*Fragrance.*—Perfume fragrance.

Reproductive organs:

*Stamens.*—Four stamens in number.
*Stamen shape.*—Filament.
*Dimensions of stamen.*—2.25 cm. in length and less than 0.50 mm. in width.
*Color of stamen.*—N155B.
*Dimensions of anther.*—1 mm. in width and 0.50 mm. in length.
*Pollen color.*—N155B.
*Amount of pollen.*—Small amount.
*Anther color.*—156A.
*Anther shape.*—Turbinate.
*Pistil.*—One.
*Color of pistil.*—N155B.
*Pistil shape.*—Filament.
*Dimensions of pistil.*—2.25 cm. in length and less than 0.50 mm. in diameter.
*Ovary position.*—Inferior.
*Ovary color.*—143A.
*Ovary shape.*—Oblong.
*Ovary dimensions.*—2 mm. in diameter and 6 mm. in length.
*Ovary surface.*—Puberulent.

Seed: No seed has been observed to date.

What is claimed is:

1. A new and distinct variety of *Abelia* plant named 'Kaleidoscope' as described and illustrated.

* * * * *